US 6,592,527 B2

(12) United States Patent
Oser et al.

(10) Patent No.: US 6,592,527 B2
(45) Date of Patent: Jul. 15, 2003

(54) APPARATUS FOR MEASURING A VARIATION IN A CIRCUMFERENCE OF A BODY PART AND METHOD FOR PLETHYSMOGRAPHY

(75) Inventors: Daniel Oser, Munich (DE); Frank Christ, Inning (DE)

(73) Assignee: DOMED medical device GmbH, Inning am Ammersee (DE)

( * ) Notice: Subject to any disclaimer, the term of this patent is extended or adjusted under 35 U.S.C. 154(b) by 0 days.

(21) Appl. No.: 10/085,228

(22) Filed: Feb. 28, 2002

(65) Prior Publication Data

US 2002/0082505 A1 Jun. 27, 2002

Related U.S. Application Data

(63) Continuation-in-part of application No. 09/051,329, filed as application No. PCT/EP97/03409 on Jun. 30, 1997, now Pat. No. 6,375,620.

(30) Foreign Application Priority Data

Aug. 9, 1996 (DE) ........................................ 196 32 263

(51) Int. Cl.$^7$ ................................................. A61B 5/02
(52) U.S. Cl. ....................................................... 600/481
(58) Field of Search ................................. 600/300–301, 600/481, 484, 490–491, 499, 587, 592, 595, 529–532, 507, 506; 606/102, 201–203; 33/555, 555.4, 2 R, 331; 73/1.73, 53.04, 61.73, 149, 861, 195, 227, 272 R, 273, 379.01–379.09, 426–429, 431; 128/845, 897–898

(56) References Cited

U.S. PATENT DOCUMENTS 3,847,142 A * 11/1974 Williams, Jr. et al. ...... 600/507
4,144,878 A    3/1979 Wheeler
4,441,504 A *  4/1984 Peterson et al. ............. 600/490
4,452,252 A *  6/1984 Sackner ....................... 600/484
4,718,426 A    1/1988 Russell

FOREIGN PATENT DOCUMENTS

DE           32 23 711 A1 *  5/1984  ............ A61B/5/10

* cited by examiner

Primary Examiner—Max F. Hindenburg
Assistant Examiner—Michael Astorino
(74) Attorney, Agent, or Firm—Wood, Phillips, Katz, Clark & Mortimer

(57) ABSTRACT

An apparatus for measuring a variation in a circumference of a body part comprising an elongated force transmission element, an elongated support element, a casing, and a displacement measuring device, said force transmission element having a first end and a second end and not being expandable longitudinally, said support element having a first end and a second end and being expandable longitudinally, said force transmission element being slidingly arranged on said support element, said displacement measuring device having force connecting means being connectable or connected to said first end of said force transmission element and being moveable relative to said casing, and comprising support connecting means being connectable or connected to said first end and to said second end of said support element, and further comprising fixing means being connectable or connected to said second end of said force transmission element and being fixed relative to said casing, said displacement measuring device having measurement means for measuring a relative movement between said force connecting means and said casing.

9 Claims, 3 Drawing Sheets

APPARATUS FOR MEASURING A VARIATION IN A CIRCUMFERENCE OF A BODY PART AND METHOD FOR PLETHYSMOGRAPHY

CROSS-REFERENCE TO RELATED APPLICATION

This is a continuation-in-part application of U.S. application Ser. No. 09/051,329, now U.S. Pat. No. 6,375,620, filed Jun. 15, 1998, which is a 371 of PCT/EP97/03409 filed Jun. 30, 1997.

BACKGROUND OF THE INVENTION

The present invention relates to an apparatus for measuring a variation in a circumference of a body part and method for plethysmography.

Plethysmography is a procedure which has been known for some time now and which is used for determining macro- and microvascular parameters in the extremities, such as the venous capacity, the venous reflux, the venous elasticity, the venous outflow rate, the material blood flow and the capillary filtration rate. In general, plethysmography allows qualitative and quantitative statements to be made concerning the state and function of the macro- and microvascular circulation in an extremity of a patient.

Plethysmography can be carried out in a very wide variety of ways, for example as water plethysmography, air plethysmography, impedance plethysmography, capacitance plethysmography, induction plethysmography or strain gauge plethysmography. These procedures make use of different physical phenomena for determining the state of the blood vessels in a body part. The present invention applies equally to venous compression plethysmography, where blood flow in the veins is occluded by means of a cuff, and to dynamic or functional plethysmography, where the blood flow in the body's blood vessels is influenced by exercise or maneuvers of the body.

In the prior art a form of strain gauge plethysmography concerning circumference changes in an extremity is disclosed in U.S. Pat. No. 3,847,142 (issued to Williams, Jr. et al. on Nov. 12, 1974). The apparatus described therein comprises a first cuff for the wrist to occlude the blood flow to the hand, a second cuff to be put arround the upper arm and a rubber strain gauge filled with mercury, to be put arround the largest part of the forearm to detect changes in its circumference. The strain gauge serves as one arm of a Wheatstone bridge circuit, the output voltage of which varies in a linear fashion according to the length of the strain gauge. The apparatus needs to be calibrated before use and requires two cuffs plus strain gauge; therefore it is rather difficult to operate. It also requires a strain gauge filled with mercury, which is relatively expensive and can be dangerous for the operating person in case of an accident or defect. For a patient suffering from venous disease, it would be desirable to have an apparatus for use at home, to determine the venous parameters himself. Such an apparatus should be easy to handle but at the same time reliably provide accurate measured values. It should be relatively low in costs and should not contain substances which could threaten the health of the patient or any other operating person.

SUMMARY OF THE INVENTION

It is therefore the object of the present invention to make available an apparatus for measuring a variation in a circumference of a body part and a method for plethysmography which does not have the disadvantages of the prior art.

According to the invention, there is provided an apparatus for measuring a variation in a circumference of a body part comprising an elongated force transmission element, an elongated support element, a casing, and a displacement measuring device, said force transmission element having a first end and a second end and not being expandable longitudinally, said support element having a first end and a second end and being expandable longitudinally, said force transmission element being slidingly arranged on said support element, said displacement measuring device having force connecting means for being connectable or connected to said first end of said force transmission element and being moveable relative to said casing, and having support connecting means for being connectable or connected to said first end and to said second end of said support element, and further having fixing means for being connectable or connected to said second end of said force transmission element and being fixed relative to said casing, said displacement measuring device having measurement means for measuring a relative movement between said force connecting means and said casing.

In the above paragraph, several elements are connectable or connected to other elements, because it is a question of convenience, costs and possibly other factors whether, for example, the force connecting means are connected to the first end of the force transmission element from the beginning, or whether this connection is only made by a person applying the inventive apparatus to a patient before beginning the measurement process.

It should also be noted, that the apparatus according to the invention measures a variation in a circumference of a body part, which requires a comparatively high resolution in terms of time e.g. measuring a value every 100 ms.

The present invention simplifies the procedure of plethysmography by measuring a variation in the circumference of a body part. An adjustment of the apparatus is not generally necessary, because the force transmission element is particularly adapted to the size of the body part of the patient which has to be examined.

Another distinct advantage of the present invention is, that it does not require an expensive strain gauge filled with mercury or a similar substance and therefore represents no danger to the health of the patient or the operating person. The force transmission element according to the invention is preferably a yarn made of polyester material which is relatively low in production costs, does not contain any harmful substances and is more stable than a conventional rubber strain gauge.

In a preferred embodiment of the invention said fixing means include adjustment means for varying the effective length of said force transmission element around said body part by either displacing said fixing means relative to said casing or by adding length to said force transmission element between said force connecting means and said fixing means. In case an adjustment of the apparatus has to be performed, the operator, for example the patient himself, a doctor or a nurse, successively adjusts the effective length of the force transmission element manually. The adjustment can be accomplished by a screw mechanism or a clamping mechanism. Both mechanisms may be applied to both, the displacement of the fixing means relative to the casing and to the addition of length to the force transmission element.

In another advantageous embodiment of the invention, said displacement measuring means include indicator means for indicating the correct position of said force connecting means in relation to said casing of said displacement measuring device by issuing an optical or acoustical signal.

Yet another preferred embodiment of the invention concerns a displacement measuring device, which includes inductive means for measuring said relative movement between said force connecting means and said casing.

The present invention also includes a system for venous compression plethysmography with an apparatus according to claim 1 and a cuff whose internal diameter can be varied in order to occlude blood flow in a body part.

The invention also comprises a method for plethysmography using an apparatus as described above, comprising the following steps:

a) arranging said apparatus on said body part by positioning said force transmission element and said support element around said body part, such that said first end of said force transmission element is connected to said force connecting means, that said second end of said force transmission element is connected to said fixing means, and that said first and second end of said support element are connected to said support connecting means, and b) registering by means of said measurement means of said displacement measuring device any relative movement between said force connecting means and said casing.

It is also conceivable, that between steps a) and b) of the method according to claims 8–9, a further step of adjusting by means of adjustment means the effective length of said force transmission element is integrated.

BRIEF DESCRIPTION OF THE DRAWINGS

The apparatus according to the invention and the method according to the invention are described below with reference to the figures, where.

DETAILED DESCRIPTION OF THE INVENTION

Figure 1:
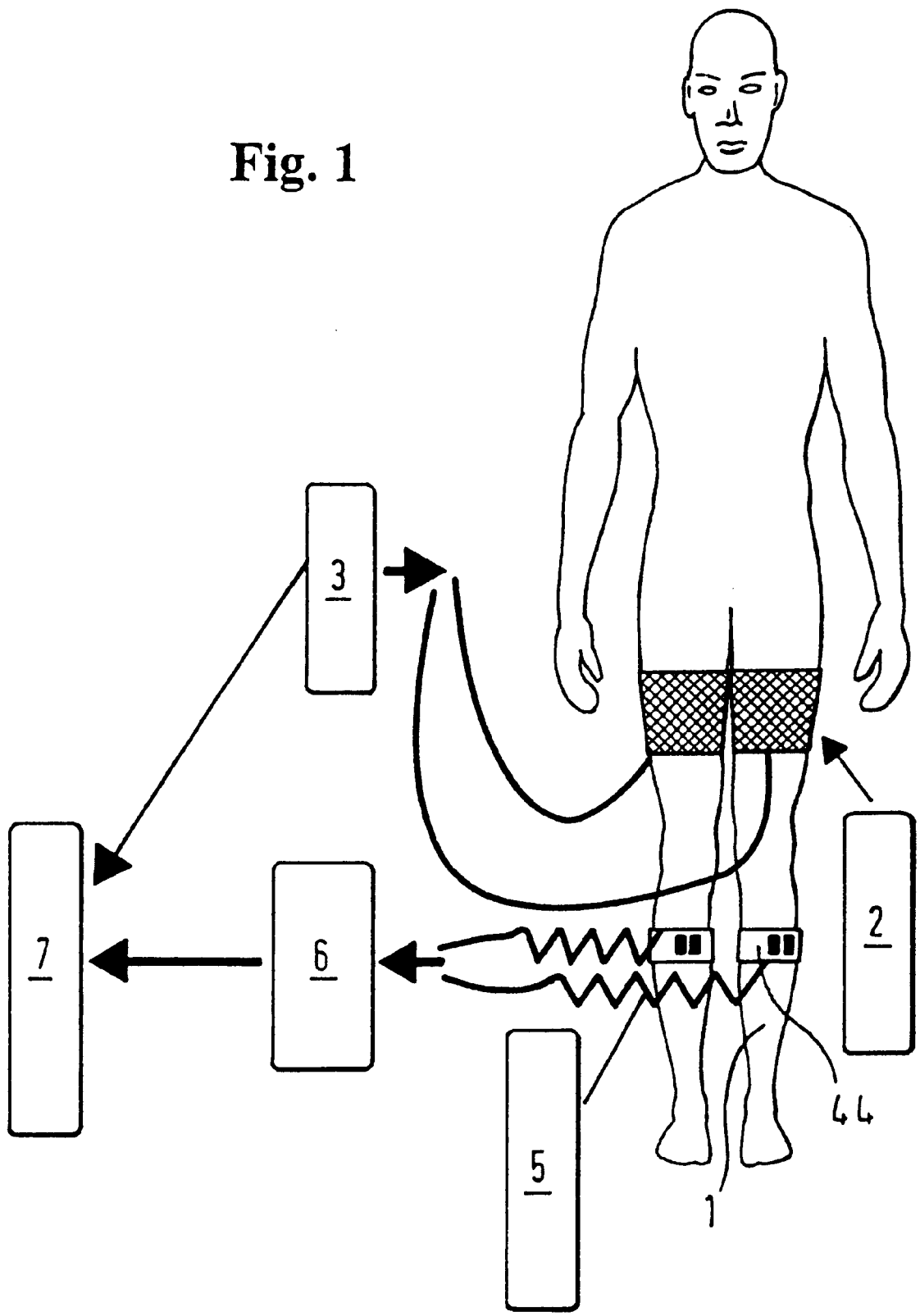
FIG. 1 shows the principle of venous compression plethysmography according to the invention.

FIG. 1 shows an apparatus 44 for venous compression plethysmography with a cuff 2 according to the invention, which encircles a body part 1, for example a leg, and whose internal diameter can be varied using a pump 3. As shown in FIG. 1, the values obtained are transferred via leads 5 to recording device 6. The signals from the recording device 6 and the pump 3 are then fed to an evaluation unit 7, where the measurement results are evaluated as a function of a measure of the change in the internal diameter of the cuff 2, generally the pressure exerted on the cuff 2 by the pump 3.

The apparatus is operated as follows: A cuff 2 is placed around the body part 1 which has to be examined. This body part can be a relatively large extremity, such as a lag or an arm, but smaller extremities, such as fingers or toes, may also be examined. When correspondingly pressurized via the pump 3, this cuff 2 generates a blockage of the returned flow of venous blood in the distally situated body part 1. The apparatus 44 is then arranged on the same body part, at a point more distant from the heart. When the body part 1 changes circumference as a result of the blood outflow obstruction which has been generated, the support element 49 is expanded, which results in a relative movement between the force connecting means 41 and the casing device 50. This relative movement is measured by inductive measurement means 58 and 59, or in other words, as a result of the relative movement a voltage is induced. This change in voltage is measured by a recording device 6 which is connected via leads 5 to both ends of apparatus 44.

The present invention may also be applied to dynamic or functional plethysmography. In this case, no cuff 2 is required to obstruct the blood flow in the blood vessels of the body part 1, since this kind of plethysmography does not require any external influence on the blood flow in the blood vessels of the body part 1.

Figure 2:
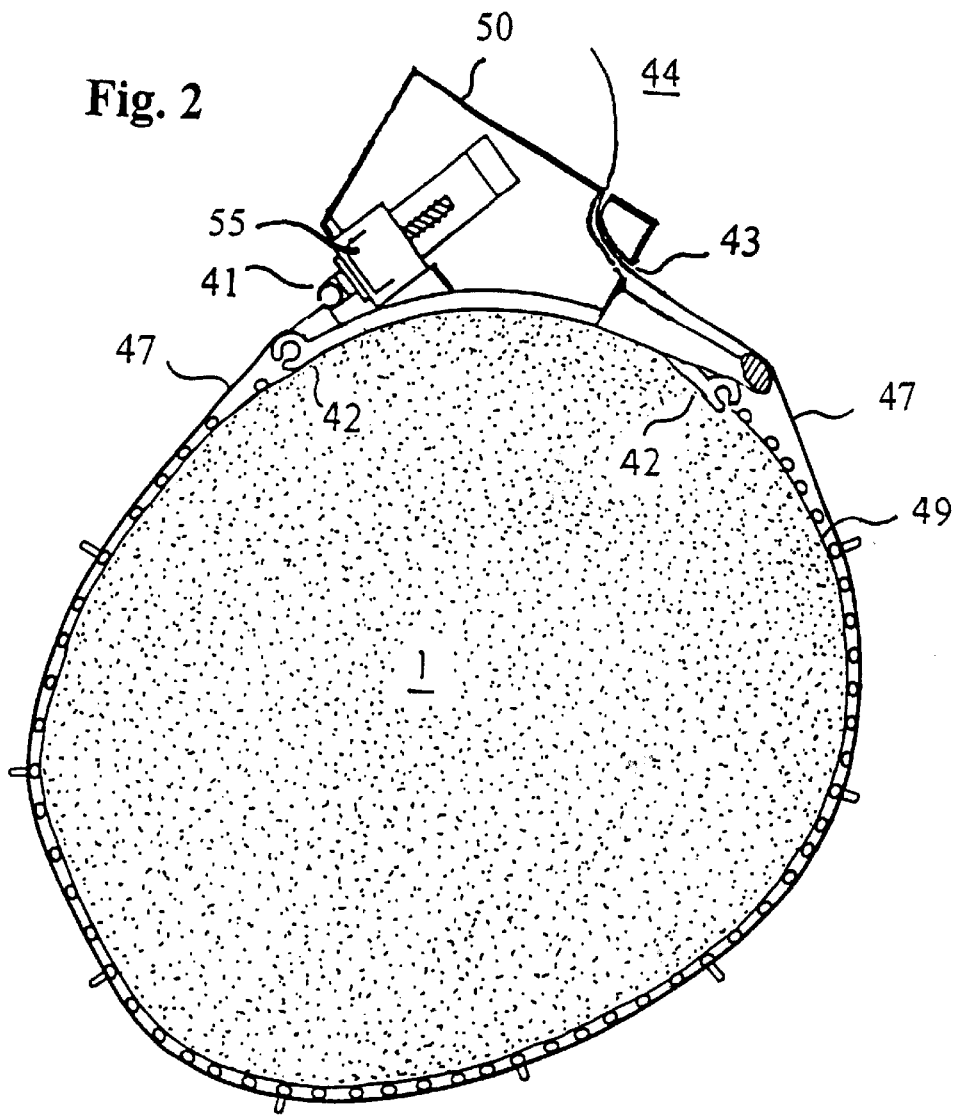
FIG. 2 shows the apparatus for measuring a variation in a circumference of a body part according to the invention.

FIGS. 2 shows a particularly preferred embodiment of the apparatus 44 according to the invention. The apparatus 44 comprises a casing 50 and a displacement measuring device 55, arranged within this casing 50, with force connecting means 41 which can be releasably connected to the first end of the force transmission element 47. The casing 50 around said displacement measuring device 55 includes support connecting means 42 for releasably connecting both ends of the support element 49. Further, the casing 50 includes fixing means 43 for being connectable to the second end of the force transmission element 47. A relative movement between the force connecting means 41 and the casing 50, which occurs in order to a circumferential change of body part 1, is measured by measurement means 58, 59. The force connecting means 41 are preferably formed ring-shaped, hook-shaped or as coupling piece whereas the support connecting means 42 are preferably formed as snap connections. The fixing means 43 are preferably formed as a clamp. Fixing means 43 may as well be formed ring-shaped, hook-shaped or as coupling piece.

Instead of being connectable, some or all of the first and second ends of the force transmission element 47 and of the support element 49 may also be rigidly connected to the respective element. Thereby, even pull-over solutions of the inventive apparatus may be realized. Finally, it is left up to the operating person, to choose which apparatus is the most convenient concerning its handling.

An adjustment of the apparatus is not necessary as long as always the same or a similarly sized body part of the same or another patient has to be examined, because the force transmission element 47 is particularly adapted to the size of that body part.

Figure 3:
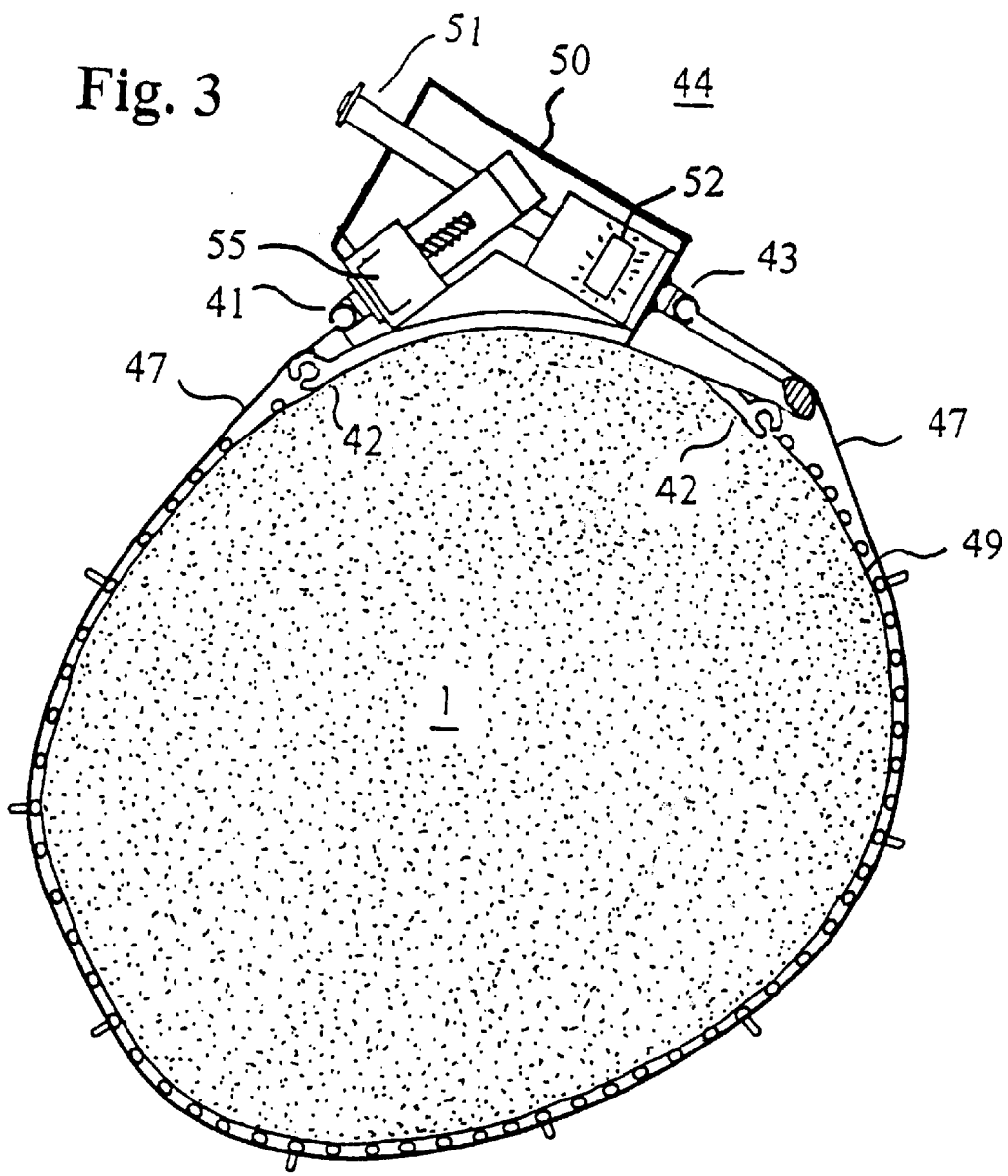
FIG. 3 shows the apparatus for measuring a variation in a circumference of a body part having adjustment means according to the invention.

FIG. 3 shows an apparatus 44 according to the invention, wherein said fixing means 43 include adjustment means 51 for varying the effective length of said force transmission element 47 between said force connecting means 41 and said fixing means 43.

The adjustment means 51 may consist of a knurled screw for expanding the force transmission element 47. The adjustment means 51 may also be formed as a clamping mechanism.

A preferred embodiment of the invention involves a casing 50 of a displacement measuring device 55 having indicator means 52 for indicating the correct position of said force connecting means 41 in relation to said casing 50. The correct position lies between the maximum and the minimum displacement of said force connecting means 41. Provided, for example, that the maximum displacement of said force connecting means 41 relative to said casing 50 would be 5 mm, the correct position on a scale from −2.5 mm to +2.5 mm would be 0.

As long as the force connecting means 41 are not positioned correctly in relation to said casing 50, the indicator means 52 do not send out any signals. When said force connecting means 41 finally get into the correct position, the indicator means 52 issue optical signals to inform the operating person of the fact, for example by means of a display or a LED. Acoustical warnings, such as a beep tone from an integrated speaker, are also conceivable.

Figure 4:
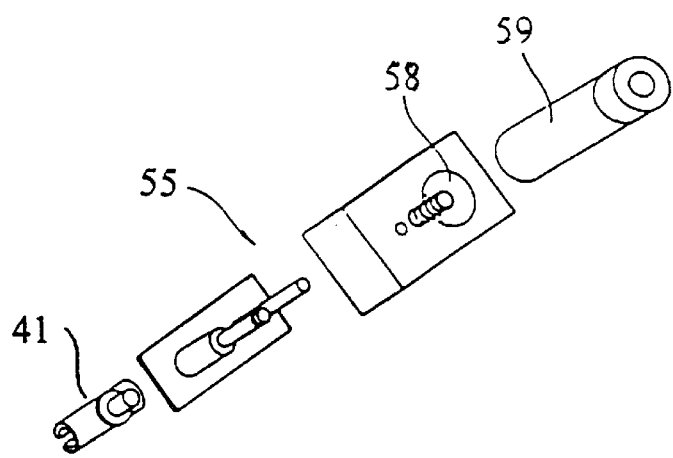
FIG. 4 shows an exploded view of the displacement measuring device according to the invention.

FIG. 4 shows an exploded view of the individual structural units of the displacement measuring device 55 according to the invention. It consists of measurement means 58 and 59, whereby the cylinder 59 is moved in the bore 58 and by means of this movement, an induction voltage is induced, i.e. the relative movement is in relation to said induced voltage. Another design of the displacement measuring device 55 of the apparatus 44 according to the invention is also possible, for example piezoelectronic sensors which can deliver a corresponding signal, or optic displacement measuring devices which can measure distances, for example by incremental transmitters.

Figure 5:
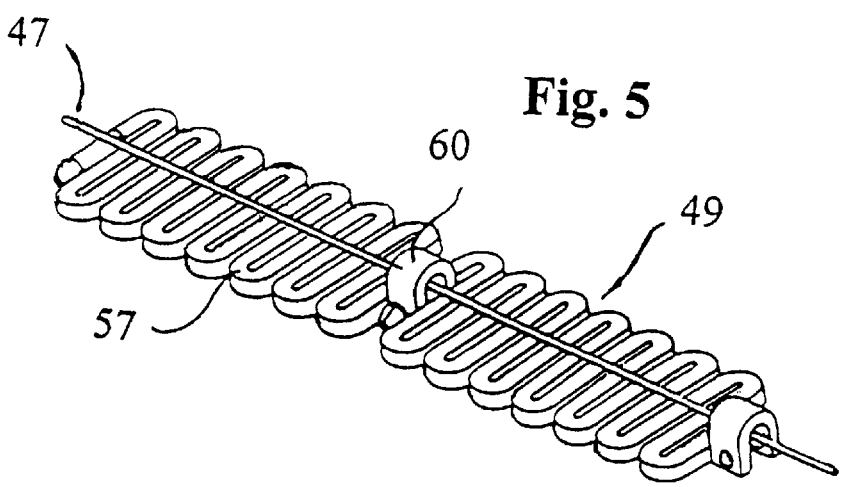
FIG. 5 shows a perspective view of the support element according to the invention.

FIG. 5 shows the preferably band-shaped support element 49 according to the invention which serves as a bearing on the skin of the extremity 1 and is designed such that it affords a reliable fit on the surface of the skin, so that it is possible to prevent the apparatus from slipping. To achieve optimum fit, force connecting means 41 always exert tension on force transmission element 47 and consequently on support element 49. To prevent force transmission element 47 from cutting in, i.e. compressing body part 1, the surface of support element 49 is relatively large.

The support element 49 preferably has a meandering cross-section which extends in the longitudinal direction. By means of this meandering configuration, the support element 49 can be expanded in the longitudinal direction upon tensile loading, and carry along the guide devices 60 located on the top surface. The guiding of the force transmission element 47 is thus at all times reliable and essentially free from friction, which is decisive for obtaining accurate values.

The support element 49 moreover has modular individual elements 57 which can be connected to one another by a releasable snap connection in such a way that the length of the support element 49 can be adjusted as desired, in order to take account of the conditions of different extremities. For the safe and reliable guiding of the force transmission elements 47, the modular individual elements 57 have devices which are preferably of circular design.

The force transmission element 47 is preferably a yarn made of polyester material which is further distinguished by a smooth and a thus low friction surface. Other materials are also possible for the force transmission member 47, for example polyamine yarns or carbon fibers.

The apparatus according to the invention affords the requirements necessary for simply, safely, cost-efficiently and reliably determining the absolute values of microvascular parameters and also of their periodic fluctuations.

What is claimed is:

1. An apparatus (44) for measuring a variation in a circumference of a body part (1) comprising an elongated force transmission element (47), an elongated support element (49), a casing (50), and a displacement measuring device (55), said force transmission element (47) having a first end and a second end and not being expandable longitudinally, said support element (49) having a first end and a second end and being expandable longitudinally, said force transmission element (47) being slidingly arranged on said support element (49), said displacement measuring device (55) having force connecting means (41) being connectable or connected to said first end of said force transmission element (47) and being moveable relative to said casing (50), and comprising support connecting means (42) being connectable or connected to said first end and to said second end of said support element (49), and further comprising fixing means (43) being connectable or connected to said second end of said force transmission element (47) and being fixed relative to said casing (50), said displacement measuring device (55) having measurement means for measuring a relative movement between said force connecting means (41) and said casing (50).

2. An apparatus (44) according to claim 1, wherein said fixing means (43) include adjustment means (51) for varying the effective length of said force transmission element (47) around said body part (1) by at least one of the following measures:

by displacing said fixing means (43) relative to said casing (50); by adding length to said force transmission element (47) between said force connecting means (41) and said fixing means (43).

3. An apparatus (44) according to claim 2, wherein said adjustment means (51) comprise at least one of the following mechanisms for adjusting said effective length of said force transmission element (47): a screw mechanism, a clamping mechanism.

4. An apparatus (44) according to claim 1, wherein said displacement measuring device (55) includes indicator means (52) for indicating the correct position of said force connecting means (41) in relation to said casing (50) of said displacement measuring device (55).

5. An apparatus (44) according to claim 4, wherein said indicator means (52) issue an optical signal or an acoustical signal, if said force connecting means (41) are positioned correctly in relation to said casing (50) of said displacement measuring device (55).

6. An apparatus (44) according to claim 1, wherein said displacement measuring device (55) includes inductive means (58, 59) for measuring said relative movement between said force connecting means (41) and said casing (50).

7. A system for venous compression plethysmography, comprising an apparatus (44) according to claim 1 and a cuff (2) whose internal diameter can be varied in order to occlude blood flow in a body part (1).

8. A method for plethysmography using an apparatus (44) according to claim 1, comprising the following steps:

a) arranging said apparatus (44) on said body part (1) by positioning said force transmission element (47) and said support element (49) around said body part (1) such that said first end of said force transmission element (47) is connected to said force connecting means (41), that said second end of said force transmission element (47) is connected to said fixing means (43), and that said first and second end of said support element (49) are connected to said support connecting means (42), b) registering by means of said measurement means of said displacement measuring device (55) any relative movement between said force connecting means (41) and said casing (50) of said displacement measuring device (55).

9. A method according to claim 8, comprising between steps a) and b) the further step of adjusting by means of adjustment means (51) the effective length of said force transmission element (47) around said body part (1).

* * * * *